(12) United States Patent
Mürner et al.

(10) Patent No.: US 8,172,840 B2
(45) Date of Patent: May 8, 2012

(54) EXTERNAL FIXATION COMPONENT

(75) Inventors: Beat Mürner, Reichenbach (CH);
Robert Wider, Derendingen (CH);
Roland Thomke, Bellach (CH); Usha Mathur, New Delhi (IN); Umesh Verma, Delhi (IN)

(73) Assignee: Stryker Trauma SA (CH)

( * ) Notice: Subject to any disclaimer, the term of this patent is extended or adjusted under 35 U.S.C. 154(b) by 238 days.

(21) Appl. No.: 12/653,975

(22) Filed: Dec. 21, 2009

(65) Prior Publication Data

US 2011/0066151 A1 Mar. 17, 2011

(30) Foreign Application Priority Data

Sep. 11, 2009 (EP) .................................. 09 170 102

(51) Int. Cl.
*A61B 17/00* (2006.01)
(52) U.S. Cl. ............ 606/54; 606/59; 403/384; 403/385; 403/289
(58) Field of Classification Search ............... 606/54–59; 403/384, 385, 395, 289
See application file for complete search history.

(56) References Cited

U.S. PATENT DOCUMENTS

| | | |
|---|---|---|
| D255,713 S | 7/1980 | Sturges |
| 5,160,335 A | 11/1992 | Wagenknecht |
| 5,304,177 A | 4/1994 | Pennig |
| 5,358,504 A | 10/1994 | Paley et al. |
| 5,376,091 A | 12/1994 | Hotchkiss et al. |
| 5,443,465 A | 8/1995 | Pennig |
| 5,662,651 A | 9/1997 | Tornier et al. |
| 5,752,954 A | 5/1998 | Mata et al. |
| 5,846,245 A | 12/1998 | McCarthy et al. |
| 5,891,144 A | 4/1999 | Mata et al. |

(Continued)

FOREIGN PATENT DOCUMENTS

EP 0700664 A1 3/1996

(Continued)

OTHER PUBLICATIONS

Kinbrum "The PEEK of Large Joint Performance?", Orthopedic Design & Technology, pp. 51-55, Mar./Apr. 2009.

(Continued)

*Primary Examiner* — Eduardo C Robert
*Assistant Examiner* — Ellen C Hammond
(74) *Attorney, Agent, or Firm* — Lerner, David, Littenberg, Krumholz & Mentlik, LLP

(57) ABSTRACT

An external fixation component includes two capture members adapted to capture independently a first and a second element of an external fixation system. A rotation member is provided between the two capture members, coupled to both capture members such that the coupling allows the two capture members to rotate about three axes relative to each other. Each capture member comprises a central locking screw extending therethrough and defining a longitudinal axis of the associated capture member. The rotation member comprises two rotation blockers, each blocker providing one interface surface adapted to be in contact with a complementary interface surface of one of the capture members, each blocker further provides a surface opposite to the interface surface comprising an inner cylindrical surface. The rotation member comprises a central disc element forming a rolling surface as complementary surface to the inner cylindrical surface of the corresponding rotation blocker. The rotation member comprises two nuts, wherein each nut is associated to one locking screw of a corresponding capture member. Each locking screw of a capture member extends through the corresponding rotation blocker and engages the corresponding nut for an individual locking of each capture member.

17 Claims, 9 Drawing Sheets

U.S. PATENT DOCUMENTS

| | | | |
|---|---|---|---|
| 6,019,769 | A | 2/2000 | McCarthy et al. |
| 6,080,153 | A | 6/2000 | Mata et al. |
| D455,831 | S | 4/2002 | Koros et al. |
| 6,409,729 | B1 | 6/2002 | Martinelli et al. |
| 6,520,962 | B1 | 2/2003 | Taylor et al. |
| 6,702,814 | B2 * | 3/2004 | Walulik et al. ............... 606/57 |
| 6,872,209 | B2 * | 3/2005 | Morrison .................. 606/278 |
| 7,004,943 | B2 | 2/2006 | Ferrante et al. |
| 7,048,735 | B2 | 5/2006 | Ferrante et al. |
| D526,410 | S | 8/2006 | Phillips et al. |
| D537,939 | S | 3/2007 | Phillips et al. |
| 7,241,074 | B2 * | 7/2007 | Thomke et al. ............. 403/385 |
| 7,261,713 | B2 | 8/2007 | Langmaid et al. |
| D551,763 | S | 9/2007 | Phillips et al. |
| 7,282,052 | B2 | 10/2007 | Mullaney |
| 7,479,142 | B2 | 1/2009 | Weiner et al. |
| 7,562,855 | B2 | 7/2009 | Oetlinger |
| 7,578,822 | B2 | 8/2009 | Rezach et al. |
| 8,029,505 | B2 * | 10/2011 | Hearn et al. ............... 606/56 |
| 2001/0049526 | A1 | 12/2001 | Venturini et al. |
| 2002/0077629 | A1 * | 6/2002 | Hoffman et al. ............ 606/59 |
| 2003/0187432 | A1 | 10/2003 | Johnson et al. |
| 2003/0199738 | A1 * | 10/2003 | Yager ........................ 600/227 |
| 2004/0044344 | A1 | 3/2004 | Winquist et al. |
| 2004/0059331 | A1 | 3/2004 | Mullaney |
| 2004/0158245 | A1 | 8/2004 | Chin |
| 2004/0249375 | A1 | 12/2004 | Agee et al. |
| 2005/0113829 | A1 | 5/2005 | Walulik et al. |
| 2005/0119656 | A1 | 6/2005 | Ferrante et al. |
| 2005/0240265 | A1 | 10/2005 | Kuiper et al. |
| 2006/0025703 | A1 | 2/2006 | Miles et al. |
| 2006/0039750 | A1 | 2/2006 | Thomke et al. |
| 2006/0052781 | A1 | 3/2006 | Thomke et al. |
| 2006/0052785 | A1 | 3/2006 | Augostino et al. |
| 2006/0155276 | A1 | 7/2006 | Walulik et al. |
| 2006/0167453 | A1 | 7/2006 | Hoffmann-Clair et al. |
| 2006/0229604 | A1 | 10/2006 | Olsen et al. |
| 2007/0123856 | A1 | 5/2007 | Deffenbaugh et al. |
| 2008/0188852 | A1 | 8/2008 | Matityahu |
| 2008/0215053 | A1 | 9/2008 | Thomke et al. |
| 2008/0294198 | A1 | 11/2008 | Jackson |
| 2008/0306527 | A1 | 12/2008 | Winslow et al. |
| 2009/0018541 | A1 | 1/2009 | Lavi |
| 2009/0088751 | A1 | 4/2009 | Mullaney |
| 2009/0099565 | A1 | 4/2009 | Weiner et al. |
| 2009/0228006 | A1 | 9/2009 | Mussolin et al. |
| 2009/0287212 | A1 | 11/2009 | Hirata et al. |

FOREIGN PATENT DOCUMENTS

| | | | |
|---|---|---|---|
| WO | 0247564 | A2 | 6/2002 |

OTHER PUBLICATIONS

European Search Report EP 10186847.9 dated Jan. 31, 2011.
U.S. Appl. No. 13/240,221, filed Sep. 22, 2011.
European Search Report EP 09170102, dated Feb. 18, 2010.

* cited by examiner

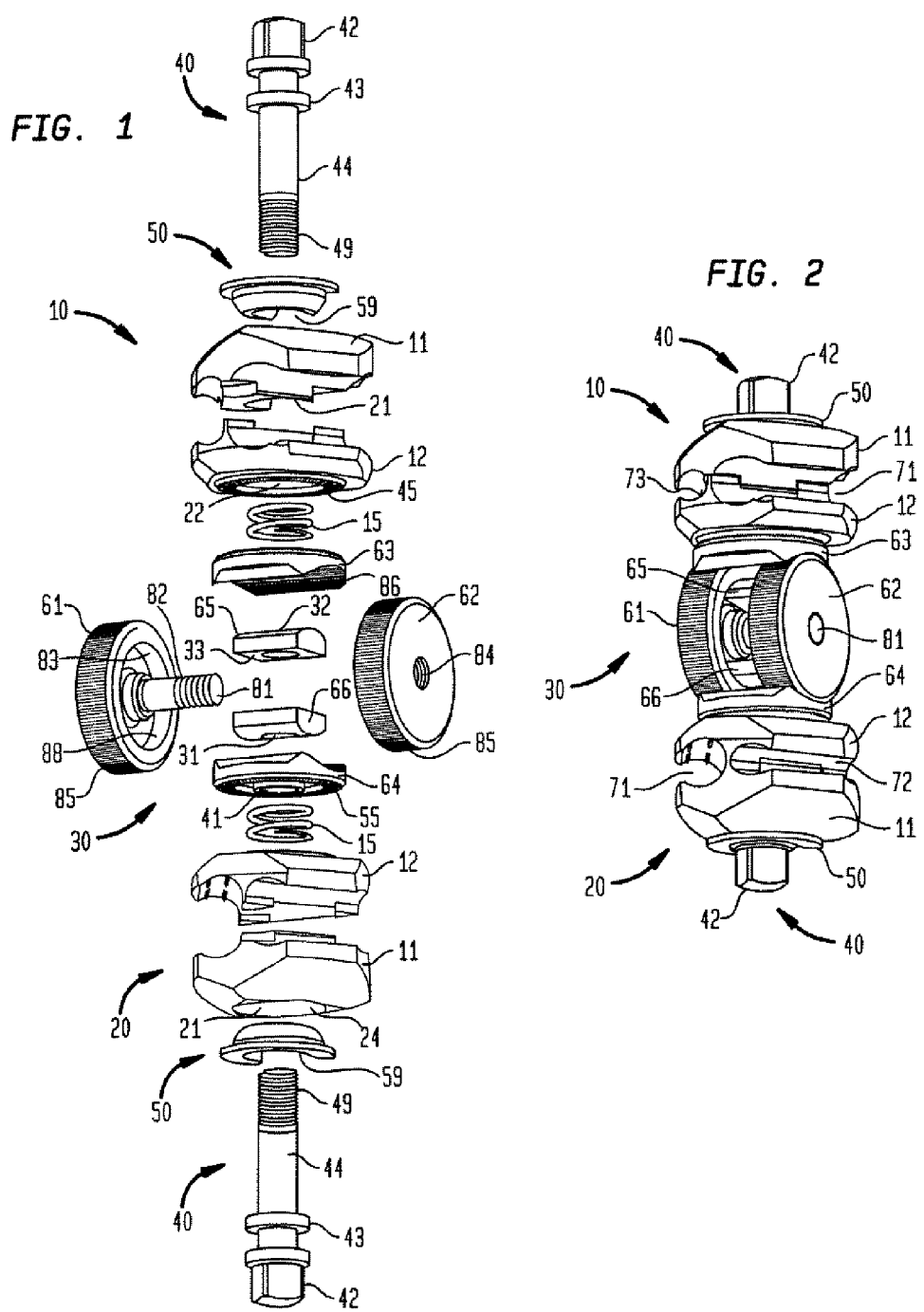

EXTERNAL FIXATION COMPONENT

This application claims the benefit of European Application No. 09 170 102.9 filed Sep. 11, 2009.

BACKGROUND OF THE INVENTION

The present invention relates to an external fixation component comprising a first capture member adapted to capture a first element of an external fixation system and a second capture member adapted to capture a second element of an external fixation system; and a rotation member, coupled to the first capture member and to the second capture member such that the coupling allows the two capture members to rotate about three axes relative to each other.

External fixation systems are widely used in orthopedics to connect two or more bone fragments to each other. Such orthopedic fixation systems comprise bone screws, pins, wires which are inserted directly into the bone material and these systems use external structural elements as fixation rods, bars and pin. In order to connect the rods and bars to form a rigid frame, different capture members and fixation clamps are used. Furthermore, fixation clamps are used to connect the screws and pins to the rigid frame to specifically hold bone fragments at an intended place.

One adjustable fixation clamp is known from U.S. Pat. Nos. 5,752,954 and 6,080,153 comprising two clamping assemblies or capture members as pairs of jaws allowing clamping of a rod as well as of a pin.

A clamping assembly for multiple rod-shaped elements is known from U.S. Patent Application Publication No. 2006/0052781 having one single pair of jaws. However, such a clamp allows clamping more than two, e.g. three or four rod-shaped elements as pins with one single clamp, thus reducing the number of clamps. However, one further fixation clamp is necessary to fix the rod of said clamp to the frame of the fixation system, usually these clamping assemblies comprise a rod which is then attached to the frame using a separate adjustable fixation clamp.

The known adjustable fixation clump of U.S. Pat. No. 5,752,954 allows two rods or elements to be clamped to be positioned in any angular position when rotated about the longitudinal axis of the device. This device does not allow inclining one clamping assembly against the other clamping assembly in view of the longitudinal axis of the device.

Another external fixation component is known from U.S. Pat. Nos. 7,004,943 and 7,048,735.

These patents relate to a combination of two capture members using a universal joint in-between wherein the coupling is adapted to secure the first and second capture members from rotation with one single activation. The single activation facilitates the handling of the device. However this device is not so versatile since the one activation element simultaneous blocks the orientation of the capture members attached to the universal joint as well as any element snapped into the capture members.

BRIEF SUMMARY OF THE INVENTION

The external fixation element according to the prior art provides a complicated rotation member which is directly connected to the capture members which element is difficult to clean and do not provide a versatile use with a plurality of different capture members.

It is therefore an objection of the invention to overcome this problem and to provide an external fixation component adapted for a variety of capture elements, especially a single rod clamp as shown in U.S. Pat. No. 5,752,954, so called multi pin clamps as shown in U.S. Patent Application Publication No. 2006/0052781, or different capture elements.

An external fixation component comprises two capture members adapted to capture independently a first and a second element of an external fixation system. Between them a rotation member is provided, coupled to both capture members such that the coupling allows the two capture members to rotate about three axes relative to each other. Each capture member comprises a central locking screw extending there through and defining a longitudinal axis of the associated capture member. The rotation member comprises two rotation blockers, each blocker providing one interface surface adapted to be in contact with a complementary interface surface of one of the capture members, each blocker further providing a surface opposite to said interface surface comprising an inner cylindrical surface. The rotation member comprises a central disc element forming a rolling surface as complementary surface to said inner cylindrical surface of the corresponding rotation blocker and it comprises two nuts, wherein each nut is associated to one locking screw of a corresponding capture member and wherein each locking screw of a capture member is extending through the corresponding rotation blocker and engages the corresponding nut for an individual locking of each capture member.

It is an advantage of the fixation element according to the invention that after having clamped one pin or rod with one clamping assembly or capture member, a practitioner willing to attach subsequently a rod to a second clamping assembly of the element can freely turn, rotate and push said second clamping assembly in any direction in the 3D space without losing the first mentioned pin or rod pre-clamped in the first capture member. It is a further advantage that due to the spring actuated first and second clamping assemblies they can be handled easily without fixed clamping and maintain the rods in place. It is especially an advantage to use the clamps having the triangular structure according to this specification allowing accommodation of different rod diameter within a single capture member. The practitioner can check the robustness of his external fixator and if he finds that the rod he has used is not stiff enough, he simply opens the single clamping assembly containing said rod, removes said thinner rod, turns the clamping assembly by 120 degrees in one or the other direction around the longitudinal axis of said capture member and snaps and clamps a new thicker fixation rod replacing the original rod.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 shows an exploded view of a first embodiment of the external fixation component of the present invention, FIG. 2 shows an assembled view of the embodiment according to FIG. 1, FIG. 4 shows a cross-section of the embodiment according to FIG. 1 along line 4-4 in FIG. 3.

DETAILED DESCRIPTION

FIG. 1 shows an exploded view of a first embodiment of the external fixation component of the present invention. The external fixation component comprises three elements. There is a first capture member 10 which is a clamping assembly. First capture member 10 is connected to a central rotation system 30 which is in turn connected to the second capture member 20, being a second clamping assembly. As will be seen in connection with FIGS. 8 and 9, different capture members can be used in connection with the central rotation member 30 as well as clamping assemblies from prior art if an adapted central locking screw and shaft is used.

Figure 4:
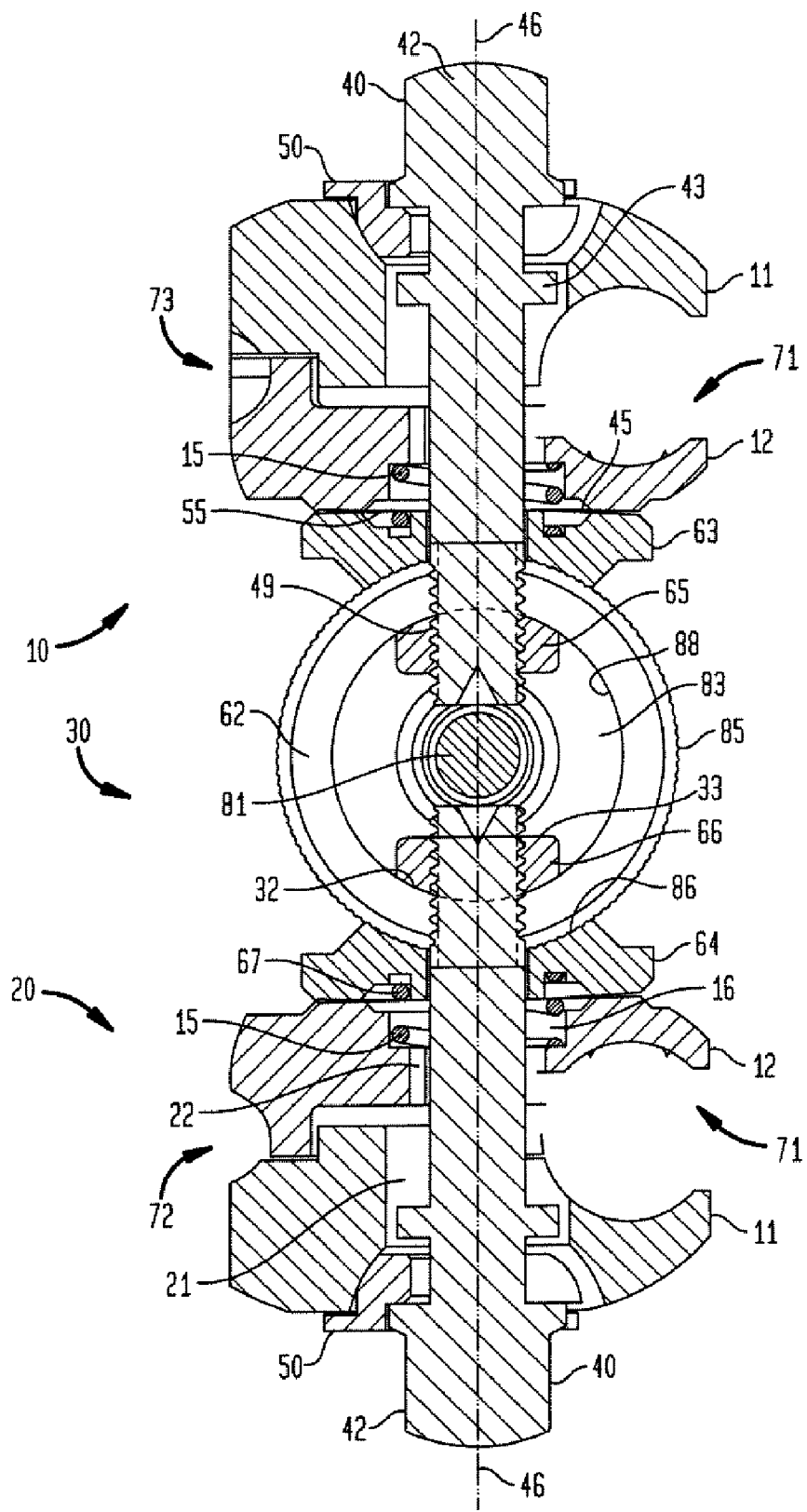
FIG. 4 shows a cross-section of the embodiment according to FIG. 1 along line 5-5 in FIG. 3.
Figure 5:
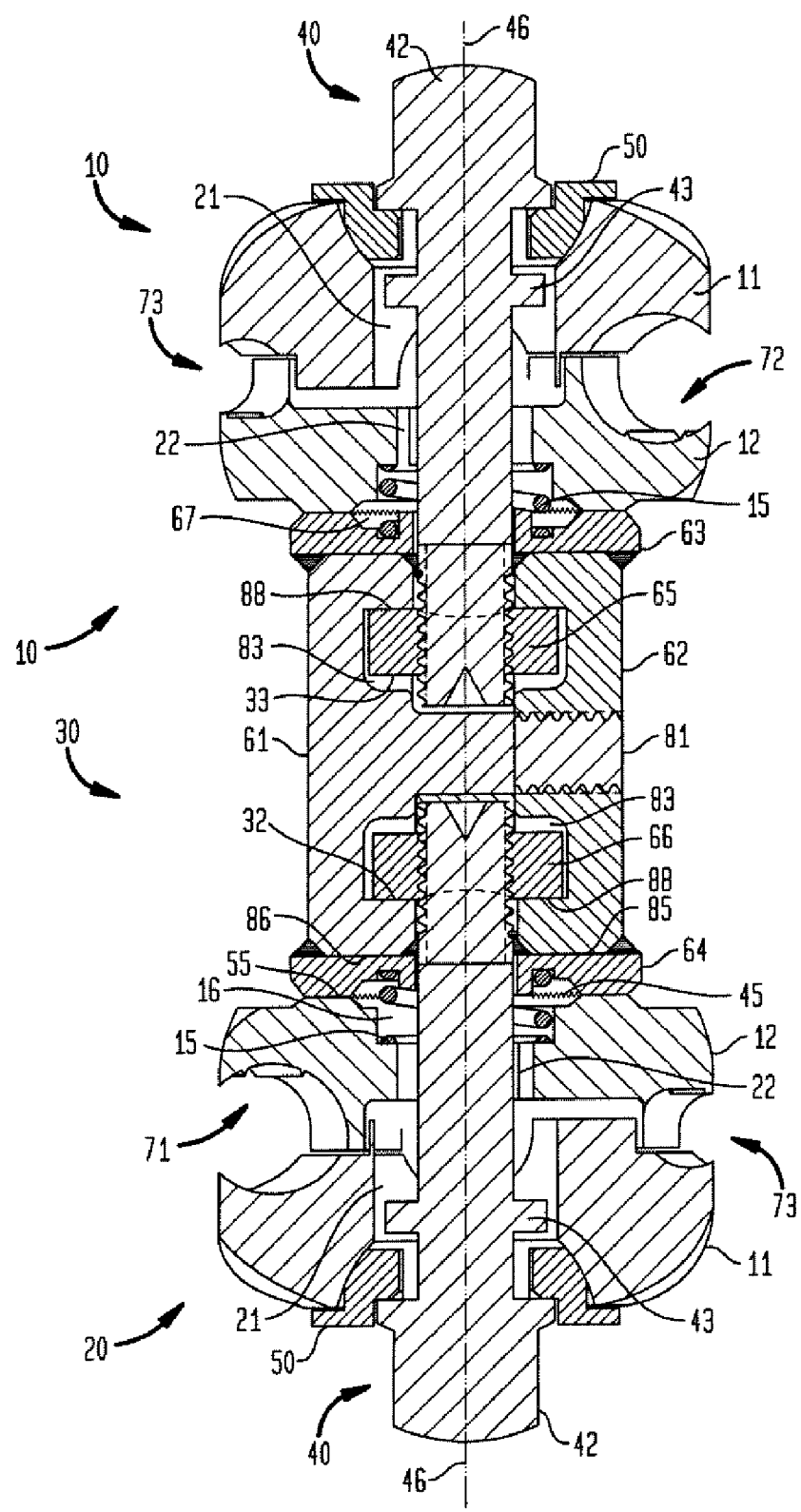

The first capture member 10 comprises a first jaw 11 and a second jaw 12 having central bores 21 and 22, respective. A screw 40 with a central shaft for locking the clamping assembly 10 is introduced through said bores 21 and 22. Shaft 40 enters the first jaw through a locking element 50 which is lodged in the rounded recess 24 of first jaw 11. The shaft 40 comprises a head 42 for actuating the screw, a proximal flange portion 43 followed by a reduced diameter portion 44, and it ends in a thread portion 49. As can be seen in FIG. 4 or 5 central shaft 40 defines the longitudinal axis 46 of clamping assembly 10. Preferably the underside of the second jaw 12 comprises an anti rotation surface, e.g. radially oriented grooves or spines around the central bore 22. This could also be a hard foam insert having such a surface 45 or another specific inlay.

The second capture member 20 of the embodiment according to FIG. 1 comprises identical features compared to the first capture member 10 within this embodiment. Therefore a specific description of second capture member 20 is omitted.

FIG. 2 shows an assembled view of the embodiment according to FIG. 1, within which it can be seen, that each capture member 10 and 20 comprise three different receptions 71, 72 and 73 for accommodating different sized rods or pins of an external fixator system.

The two capture members 10 and 20 are connected via the thread portion 49 of the screw with central rotating system 30. The rotation member 30 comprises a central disc or wheel 61 having a shaft 81 and a complementary disc or wheel 62 comprising an inner central bore 84 to accommodate shaft 81 with its outer thread 82. Shaft 81 defines the rotational axis of the discs 61, 62 of rotation system 30. The longitudinal axes 46 of both capture members 10 and 20, connected by the rotation system 30, intersect in the middle between the discs 61 and 62 on the axis defined by shaft 81. Shaft 81 is thus oriented perpendicular to the plane spanned by the axes 46. Preferably the width defined by the distance between the discs 61 and 62 is not larger than the dimension of the capture members 10 and 20 around axis 46.

Shaft 81 can be adapted to provide an inner abutment surface, when disc 62 is completely screwed on disc 61. It is also possible that the connection between discs 61 and 62 is glued, soldered, riveted etc. It is not necessary that the discs 61 and 62 can be separated but could be band shaped. In a different embodiment shaft 81 can also be non-unitary with disc 61 and therefore both discs 61 and 62 would be attached at shaft 81. The outer rolling surface 85 of the discs 61 and 62 is preferably made up or covered by an anti rotation surface, e.g. grooves or spines tangential to the cylindrical surface of the discs. Thus the grooves or spines may extend in the same direction as the cylindrical axis. Both discs 61 and 62 comprise a circular ring undercut 83 oriented to the inside providing an inner cylindrical abutment surface 88 allowing introducing a first nut 65 having a central bore 31 between the discs 61, 62. The underside 33 of the first nut 65 is preferably planar as are the side surfaces, wherein the upper surface 32 is rounded complementary to the abutment surface 88 of the discs 61, 62.

The outer threaded portion 49 of the screw 40 is adapted to be screwed into a complementary inner thread within the bore 31 of the first nut 65 of rotation member 30.

Rotation member 30 is connected via first rotation blocker 63 to the first capture member 10. First rotation blocker 63 comprises an inner central bore 41 for the shaft 40 as well as a preferably level upper surface 55, at least partly complementary to the anti rotation surface 45 of the capture member 10. First rotation blocker 63 furthermore comprises an anti-rotation blocker surface 86 provided opposite to the level upper surface 55. Anti-rotation blocker surface 86 is at least a partly inner cylindrical surface having a curvature complementary to the curvature of the rolling surface of the two discs 61 and 62. Blocker surface 86 may also be grooved or splined to engage surface 85 and lock the rotation of discs 61 and 62.

The length of the shaft 40 is adapted to be screwed into the complementary inner thread within bore 31 after traversing bore 41 of the first rotation blocker 63 (and jaws 11 and 12). The length of the shaft 40 is such that, if the capture member 10 is completely closed, the bottom of screw 40 does not touch the central shaft 81 of the rotation member 30.

In the embodiment shown in FIGS. 1 and 2, the capture members 10 and 20 each comprise a spring 15 positioned along the longitudinal axis of the screw 40 around the reduced diameter shaft 44 between the respective rotation blocker 63 or 64 and the second jaw 12. Thus it can be ensured that initially pins or rods can be readily snapped into reception openings 71, 72 and 73, since jaws 11 and 12 can be translationally pushed away one from the other and optionally pivoted against the force of the respective spring 15. Even before the capture member 11 or 12 is closed the spring 15 pushes the two blocking surfaces 85 and 86 on disc the rotation blocker 63, 64 and elements 61, 62, respectively, one towards the other.

Beside the central discs 61, 62 with shaft 81 forming the rolling surface and clamping surface providing element the rotation member 30 comprises two blocking elements 65 and 66 connected with the capture member 10 and 20, respectively, via the locking screw 40 as well as two rotation blockers 63 and 64 providing the interface surface 55 with the capture members 10 and 20, respectively.

Figure 3:
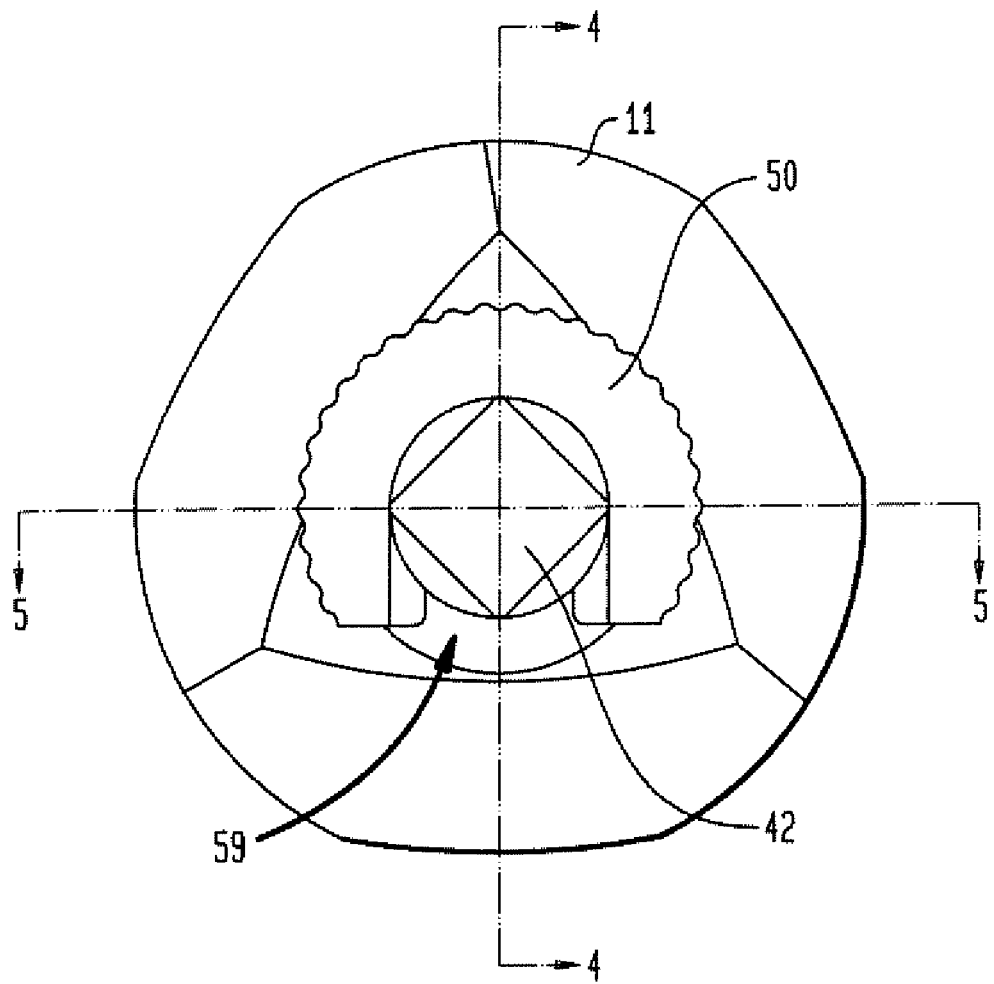
FIG. 3 shows a view from above on the embodiment according to FIG. 1.

FIG. 3 shows a view from above of the embodiment according to FIG. 1 providing visualization of the two cross-section views of FIGS. 4 and 5 along lines 4-4 and 5-5, respectively. Identical reference numerals are used for identical or similar features within all embodiments throughout all drawings.

FIG. 3 shows that locking element 50 has a lateral opening 59 allowing retrieval of the locking element 50, if the screw 40 is loosened to withdraw element 50 from the rounded recess 24. Screw 40 has a flange 43 positioned inside jaw 11 allowing a translational movement of jaw 11 and even a withdrawal of jaw 11, if the locking element 50 is removed; but second jaw 12 having a smaller dimension bore 22 cannot be removed. Therefore the fixation element 10 remains partly assembled for easy cleaning of the interstitial cavities.

Spring 15 is provided within a spring reception recess 16 in jaw 12 and within spring reception recess 67 in the rotation blocker 63 and 64, respectively. These springs 15 enable the practitioner using the element to freely rotate capture member 10 or 20 around longitudinal axis 46 and this independently for each capture member 10 or 20. In other embodiments, not shown in the drawings, there can be provided such a spring between jaws 11 and 12 of a first capture member or each capture member 10 or 20 or between rotation blockers 63, 64 and disc 61, 62 or nuts 65, 66 respectively. In such a case the rotation around the shaft axis 81 would be easily enabled, still allowing snapping in of rods into reception openings 71, 72 and 73. Spring 15 as shown in these embodiments is a compression spring. It is also possible to provide one or a pack of Belleville washers as a spring element. In other embodiments elastic foams can be used.

Rotation member 30 comprises the partly hollow discs 61 and 62, wherein the circular ring undercut 83 provides the abutment surface of the upper rounded surface 32 of the nuts 65 and 66, respectively. Although surfaces 32 are shown as cylindrical complementary to the undercut surface it is clear that said complementary surface 32 is only mandatory for the portions reaching under the disc edges, wherein the zone around the hole 31 can be configured differently. It is possible that the nuts 65 and 66 have portions reaching in the interspace between the discs up to surface 85. On the other hand it is also possible that the planar underside 33 of the nuts 65 and 66, respectively, are cylindrical or reach until the central shaft. Preferably the complementary interface surfaces 45 and 55 of the capture members 10, 20 and rotation blocker 63, 64, respectively, are essentially planar in a plane perpendicular to the axis 46 of the respective capture member 10, 20.

In one embodiment, the end portions of screw threads 49 are destroyed, so that the nut 65 or 66 cannot be removed from the screw 40 of the capture member 10 or 20, respectively. Depending on the angular coverage of the nut 65 and 66, it can then be avoided that, even by turning the nuts 65, 66 by 90 degrees around the axis 46, the nuts are removed from the space inside the discs 61, 62.

Figure 6:
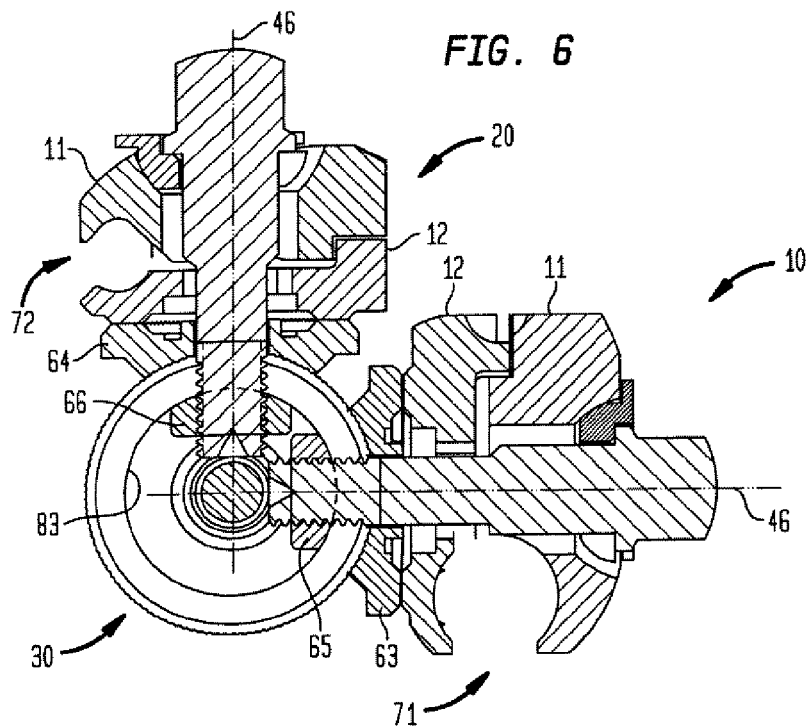
FIG. 6 shows a cross-section of a second embodiment similar to the embodiment of FIG. 1, omitting springs, wherein the capture members are rotated close one to the other.
Figure 7:
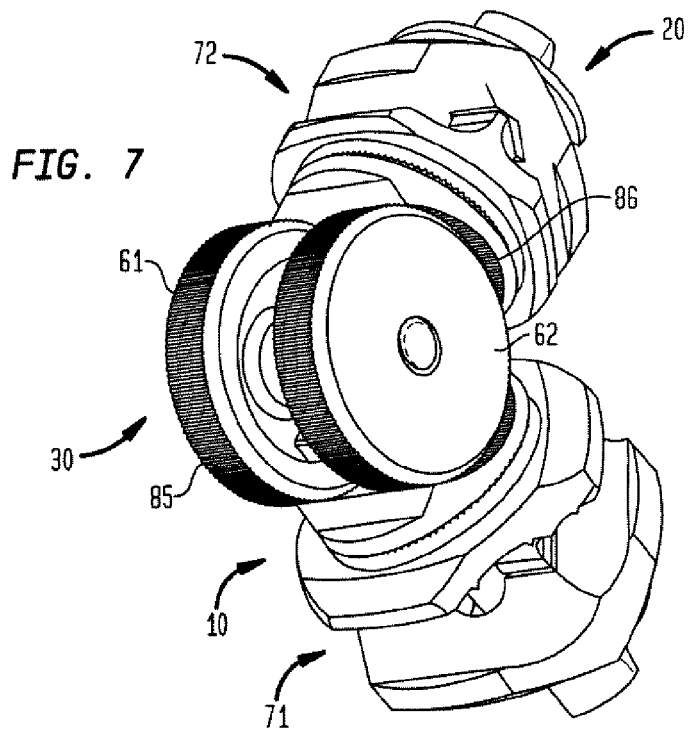
FIG. 7 shows a perspective view of the position of the element in FIG. 6.

FIG. 6 shows a cross-section of an embodiment similar to FIG. 1, but omitting the springs 15, wherein the capture members 10, 20 are rotated close one to the other. FIG. 7 shows a perspective view of the position of the external fixation element in FIG. 6. The capture members 10 and 20 are rotated in such a way that their longitudinal axes 46 are in a right angle when looking in the plane of the discs 61, 62. At this angle, the edges of the lower planar surfaces 33 of the nuts 65 and 66 come into contact and limit a further rotational movement. However, FIGS. 6 and 7 show that the external fixation element is easy to handle. A rod or pin is snapped, e.g. into reception opening 71 in first capture member 10. Then the corresponding screw 40 is slightly tightened, thus bringing the interface surfaces 45, 55 of elements 12 and 63 into a contact but still allowing a rotation of the rotation member and thus of the second capture member around axis 46 of the first capture member 10. Furthermore blocking surfaces 85 and 86 of element 63 and discs 61, 62 come into contact. It is then possible but not necessary to completely tighten the screw 40 of first capture member 10 in the angular correct position for further building of an external fixation frame. Then a second rod or pin is e.g. snapped into the reception 72 of the second capture member 20, after rotation of the second capture member around its own axis 46 (against surfaces 45, 55) as well as around the rolling surface 86 of the discs 61, 62 against the corresponding surface 85 of the element 64. Then this second screw 40 of second capture member 20 is tightened and the frame is fixed.

Figure 8:
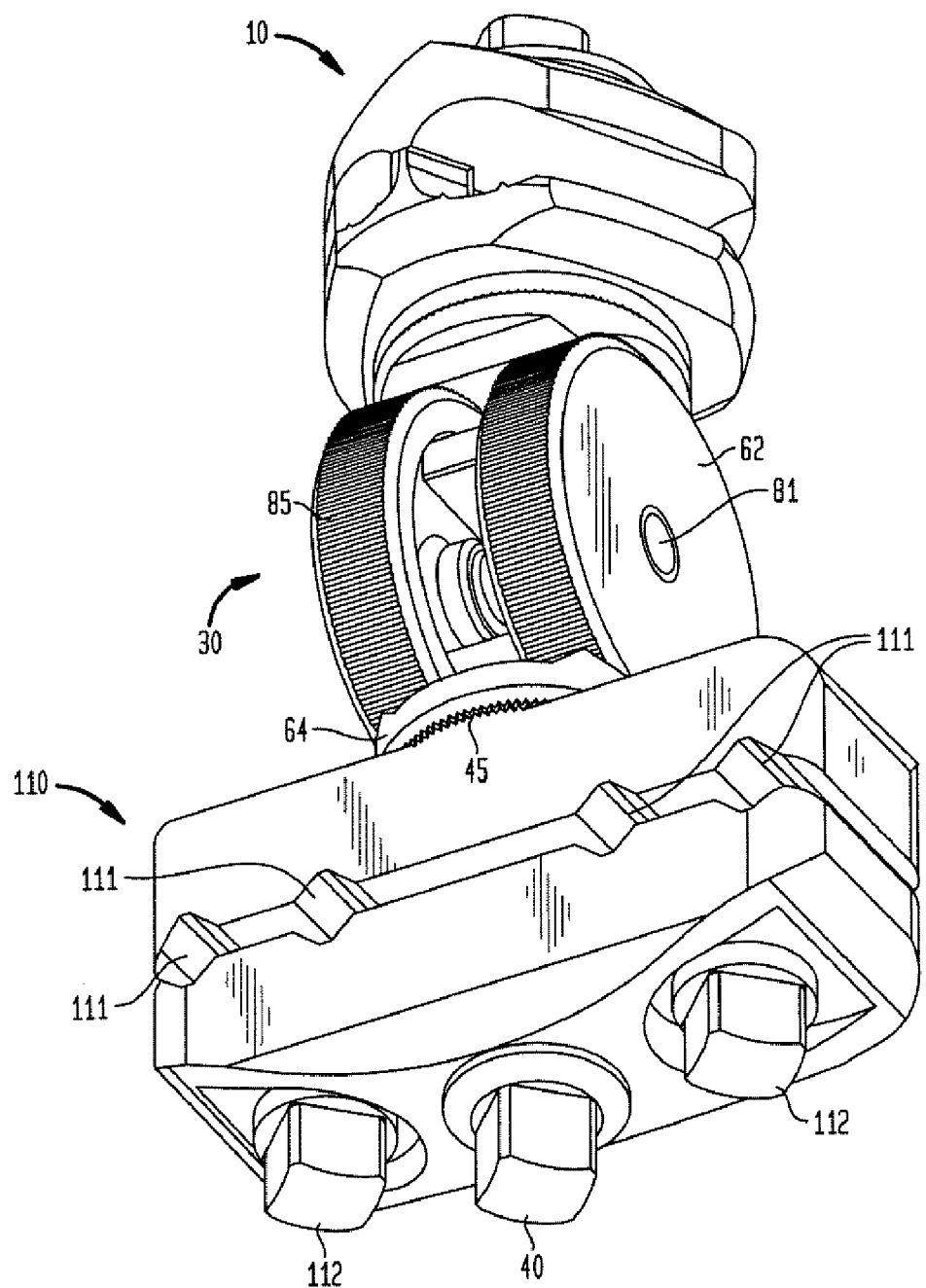
FIG. 8 shows a perspective view of a third embodiment according to the invention.

FIG. 8 shows a perspective view of a second embodiment according to the invention, wherein a further capture member 110 is provided. Said further capture member 110 is a multipin capture member having four reception openings 111 for pins. The openings 111 are provided as parallel grooves, but also oblique grooves are possible. Beside central screw 40 having the same function as in the first mentioned embodiment, there are two multipin fixation screws 112 to clamp jaws 11 and 12 of this embodiment. Lower jaw 12 comprises the anti-rotation interface surface 45 being in contact with blocking member 64 of the rotation member 30.

Figure 9:
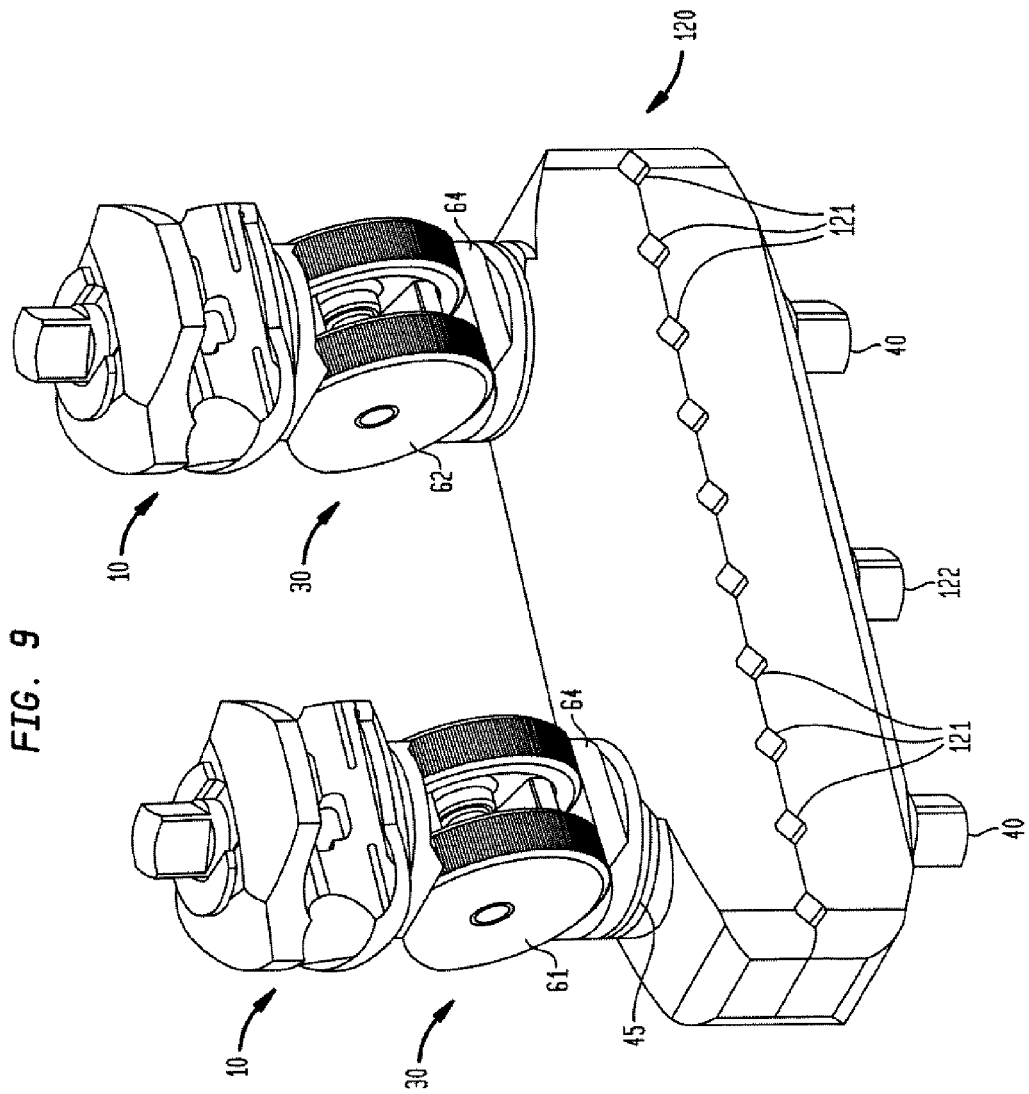
FIG. 9 shows a perspective view of a fourth embodiment of the invention.

FIG. 9 shows a perspective view of a further different embodiment of the invention, showing a different additional capture member 120. Capture member 120 is provided with a plurality of pin grooves 121 between jaws 11 and 12, wherein the multipin clamp is closed using one central multipin fixation screw 122 as well as two lateral fixation screws 40. These screws 40 are provided to attach two rotation members 30 being in contact with one first capture member 10 each, which can be oriented in any direction due to the three rotational interfaces.

Figure 10:
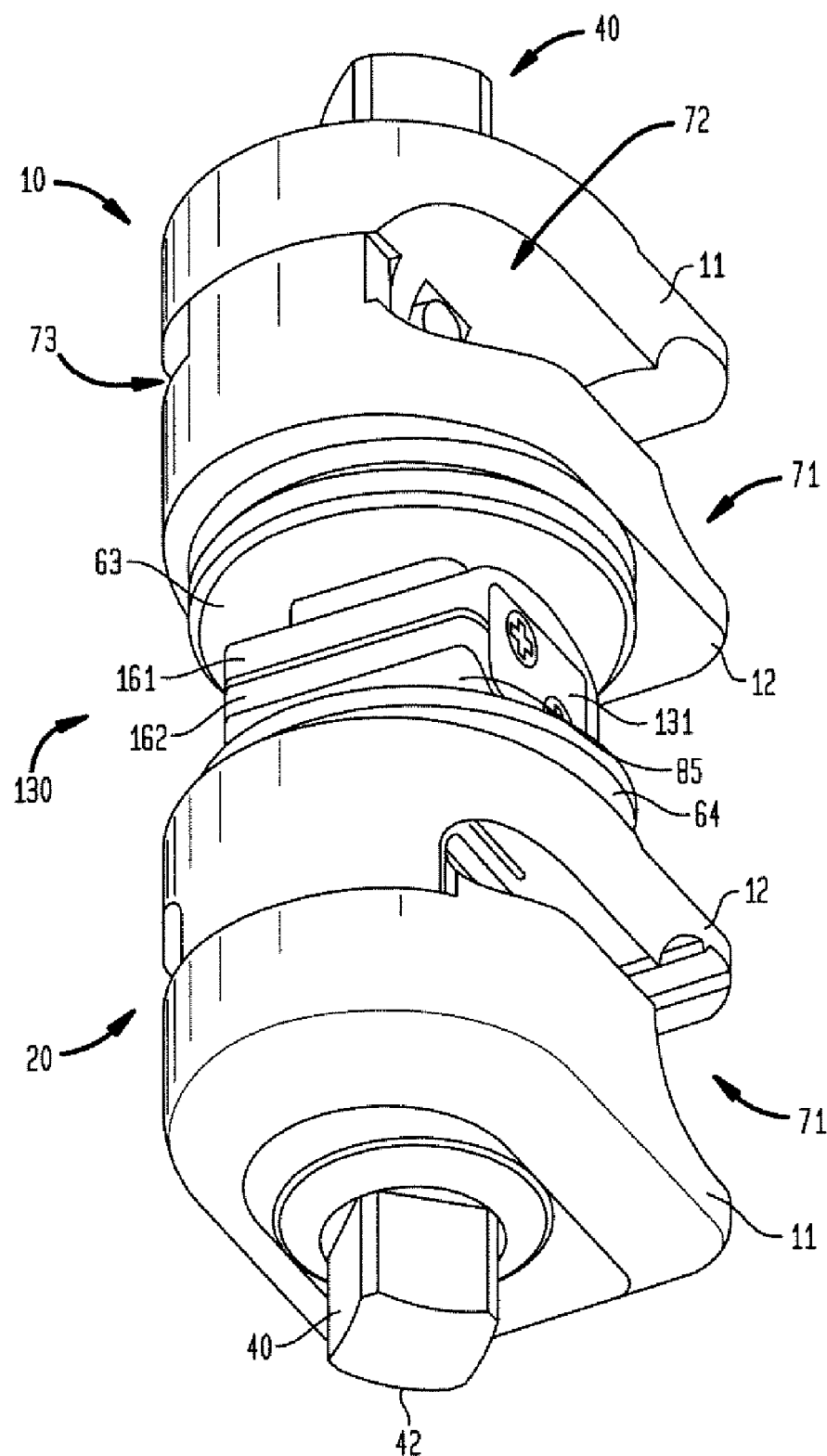
FIG. 10 shows a perspective view of a fifth embodiment of the invention.
Figure 11:
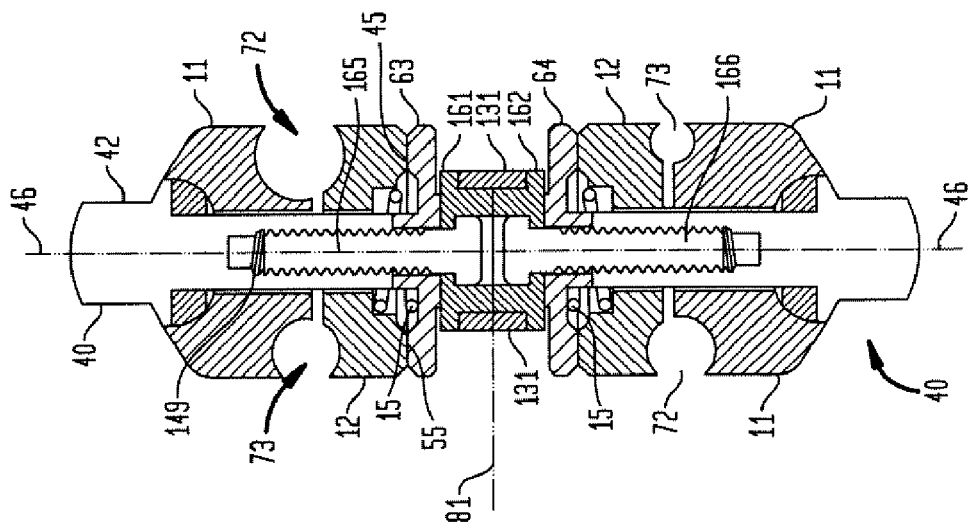
FIG. 11 shows one cross-section of the embodiment according to FIG. 10.
Figure 12:
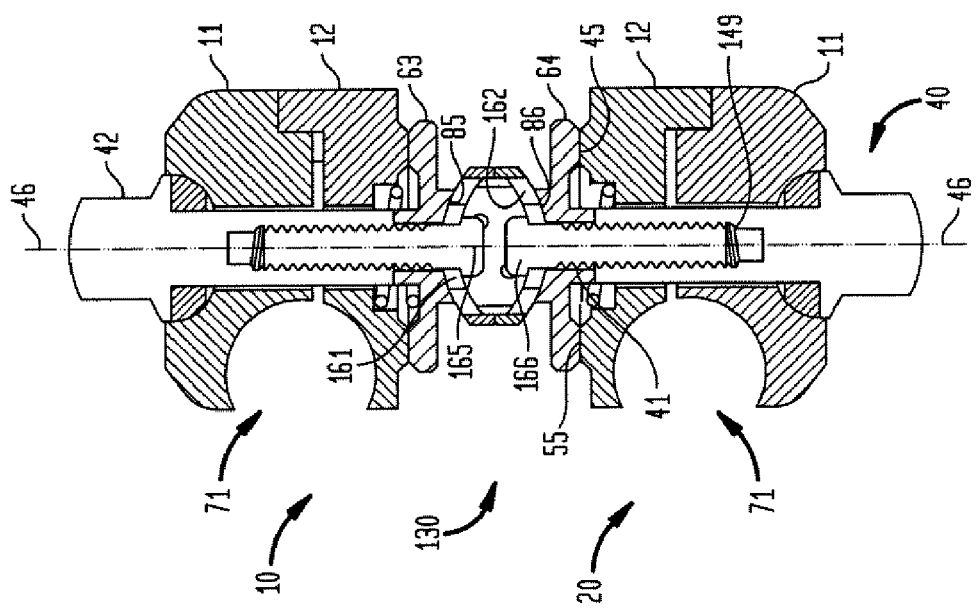
FIG. 12 shows a further cross-section of the embodiment according to FIG. 10.

FIG. 10 shows a perspective view of a fifth embodiment of the invention, wherein FIGS. 11 and 12 show cross-sections of the embodiment according to FIG. 10. The external fixation element according to FIG. 10 comprises a first capture member 10 and a second capture member 20, wherein different clamping assemblies are used, providing three different receptions 71, 72 and 73 for rods or pins. The capture members 10, 20 are connected to the rotation member 130 via central shafts 40 traversing rotation blockers 63 and 64 comprising an anti rotation blocker surface 86. The central shafts 40 comprise an internal thread for accommodating counter screws 165 and 166, respectively. Heads of the counter screws 165 and 166 are lodged in the disc elements 161, 162, respectively.

The disc elements 161 and 162 are different to the discs 61 and 62, but have the common feature of a curved outer rolling surface 85 being opposite to anti rotation blocker surface 86 in blockers 63 and 64. The two discs 161 and 162, having the form of a circular segment in cross section, are connected together via two fixation plates 131 joining the two parts. As in the embodiment shown above, a central hollow spring 15 is provided around shaft 40 between rotation blockers 63 and 64 and jaw 12. The disc elements 161 and 162 provide a circular surface to allow rotation of the corresponding capture member about an axis which is here not located in the centre axis 81 of the rotation member 130 but below and opposite the centre. This allows for a lesser height of the overall fixation element but of course restricts the possibility of any rotation. Here, the rotation can be performed by about + or −30 degrees to the left and to the right around the position shown in FIG. 11. Thus the two capture members 10 and 20 can only positioned in an angle of 120 degrees and not in an angle of 90 degree as shown in FIGS. 6 and 7.

One further difference between the embodiments of FIG. 1 and FIGS. 10-12 is the provision of a counter screw 165, 166 instead of a counter nut 65, 66. These screws 165, 166 are positioned crossing a slit within the discs 161, 162, and a through bore 41 in blockers 63 and 64, respectively, while the hollow shaft 40 abuts against an upper surface of the blocker 63 or 64. The advantage of the screws 165, 166 is that their heads are blocked from leaving the central rotation body formed by disc portions 161 and 162. Turning shaft 40 only advances the engagement of the threads of shaft 40 and screw 165, 166. Therefore, there was no advance of a thread into the rotation member and the two opposite screw heads of counter screws 165, 166 are positioned quite near one to the other. However, shaft 40 is still called a central locking screw 40 since the shaft comprises an inner thread 149. Therefore element 40 provides a screw in connection with counter screw 165, 166.

In one of the embodiments of the drawings the combination screw 40 and counter nut 65, 66 is used with the (cylindrical) disc elements 61 and 62, and in a different embodiment the shaft 40 and counter screws 165, 166 is used with the (circular segment) disc elements 161 and 162, it is clear for some one skilled in the art that the screw 40+counter nut 65 combination can be used with the discs 161, 162 and the shaft 40+counter screw 165 combination can be used with the discs 61, 62.

The external fixation element comprising the capture members 10, 20, 110 and 120 are made e.g. in stainless steel, titanium, ceramics or plastics depending on the application field of the external fixation element. The receptions 71, 72, 73, 111, 121 can accommodate different sized pins, rods, bars, Schanz screws or Kirschner wires, depending on the application of the external fixation element (upper limbs, lower limbs, size of the patient etc.).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation component comprising
a first capture member adapted to capture a first element of an external fixation system; and
a second capture member adapted to capture a second element of an external fixation system; and
a rotation member, coupled to the first capture member and to the second capture member such that the coupling allows the two capture members to rotate about three axes relative to each other,
wherein each capture member comprises a central locking screw extending there through and defining a longitudinal axis of the associated capture member,
wherein the rotation member comprises
two rotation blockers;
a central disc element; and
two counter elements;
wherein each rotation blocker provides one interface surface adapted to be in contact with a complementary interface surface of one of the capture members,
wherein each rotation blocker comprises a surface opposite to said interface surface comprising an inner cylindrical surface,
wherein the central disc element of the rotation member forms an outer rolling surface as complementary surface to the inner cylindrical surface of the corresponding rotation blocker allowing rotation of the corresponding capture element around an axis of the central disc element, and
wherein each counter element is associated to one of said locking screw of a corresponding capture member and wherein each locking screw of a capture member is extending through the corresponding rotation blocker and engages the corresponding counter element for an individual locking of each capture member.

2. The external fixation component according to claim 1, wherein the counter element is a nut and the locking screw comprises an outer thread for the locking engagement with the nut, wherein each nut comprises a central bore having a thread to accommodate the locking screw of the corresponding capture member.

3. The external fixation component according to claim 1, wherein the counter element is a counter screw and the locking screw comprises an inner thread for the locking engagement with the counter screw.

4. The external fixation component according to claim 1, wherein the central disc element comprises a central axis and two lateral cylindrical discs defining an interspace between them, wherein each cylindrical disc comprises a circular ring undercut to accommodate lateral parts of the counter elements in said interspace, wherein each counter element has a cylindrical segment as upper surface to block, upon tightening of the associated screw, the interface surfaces between the capture member and the rotation blocker as well as the upper surface and the undercut against a rotational movement around the corresponding axes.

5. The external fixation component according to claim 1, wherein the central disc element comprises an upper and a lower disc having the form of a circular segment in cross-section having a slit in the circumference of said segment to accommodate the flange surface of a counter element; wherein each counter element has a cylindrical segment as upper surface to block, upon tightening of the associated screw, the interface surfaces between the capture member and the rotation blocker as well as the upper surface and the undercut against a rotational movement around the corresponding axes.

6. The external fixation component according to claim 1, wherein said interface surfaces between the capture member and the rotation blocker are perpendicular to said longitudinal axis for a rotation about said axis.

7. The external fixation component according to claim 1, wherein the interface surfaces between the capture member and the rotation blocker comprise radial grooves around the central through going bore in the capture member as well as in the rotation blocker.

8. The external fixation component according to claim 1, wherein the rolling surface of the central disc element comprises engaging grooves oriented in the longitudinal direction of the shaft of the central disc element and wherein complementary grooves are provided in each rotation blocker on an inner cylindrical surface.

9. An external fixation component comprising:
a first clamp having a first pair of jaws rotatably mounted on a first axially extending shaft;
a second clamp having a second pair of jaws rotatably mounted on a second axially extending shaft, a first jaw of both the first and second pair of jaws having an anti-rotation means formed on an outwardly facing surface thereof;
first and second rotation blockers, the first blocker mounted on the first axially extending shaft and the second rotation blocker mounted on the second axially extending shaft, each blocker having an anti-rotation means formed on a first surface thereof for respectively engaging the anti-rotation surface of the first jaw of the first and second clamps, the first and second rotation blockers having an anti-rotation means formed on a second surface thereof;

a disc element having an outer cylindrical surface extending along a central axis and including an anti-rotation means, the cylindrical surface engaging the anti-rotation means on the second surface of both the first and second rotation blockers, the disc element coupled to both the first and second axially extending shafts, the central axis of the disc element cylindrical surface extending perpendicular to the axis of the first and second axially extending shafts.

10. The component as set forth in claim 9 wherein the anti-rotation means are a plurality of grooves.

11. The external fixation component as set forth in claim 9 wherein each clamp shaft comprises a locking screw extending therethrough and defining the shaft longitudinal axis of the jaws.

12. The external fixation component according to claim 11, wherein each clamp has a nut and the locking screw comprises an outer thread for the locking engagement with the nut, wherein each nut comprises a central bore having a thread to accommodate the locking screw of the corresponding clamp.

13. The external fixation component according to claim 12, wherein the disc comprises the central axis and two lateral cylindrical discs defining an interspace between, wherein each cylindrical disc comprises a circular ring-shaped undercut to accommodate a portion of each nut, wherein each nut has a cylindrical surface to block, upon tightening of the associated locking screw, interface surfaces between the discs and the rotation blocker as well as the rotation blocker and the anti-rotation means of each first jaw.

14. An external fixation component comprising:
a first clamp having a first pair of jaws rotatably mounted on a first axially extending shaft;
a second clamp having a second pair of jaws rotatably mounted on a second axially extending shaft, a first jaw of both the first and second pair of jaws having an anti-rotation means formed on an outwardly facing surface thereof;
first and second rotation blockers, the first blocker mounted on the first axially extending shaft and the second rotation blocker mounted on the second axially extending shaft, each blocker having an anti-rotation means formed on a first surface thereof for respectively engaging the anti-rotation surface of the first jaw of the first and second clamps, the first and second rotation blockers having an anti-rotation means formed on a second surface thereof;
a blocking element having an outer part-cylindrical surface extending along a central axis and the part-cylindrical surface including an anti-rotation means, the part-cylindrical surface engaging the anti-rotation means on the second surface of both the first and second rotation blockers, the blocking element coupled to both the first and second axially extending shafts, the central axis of the blocking element part-cylindrical surface extending perpendicular to the axis of the first and second axially extending shafts.

15. The component as set forth in claim 14 wherein the anti-rotation means are a plurality of grooves.

16. The external fixation component as set forth in claim 14 wherein each clamp shaft comprises a locking screw extending therethrough and defining the shaft longitudinal axis of the jaws.

17. The external fixation component according to claim 16, wherein each clamp has a threaded element and the locking screw comprises a thread for the locking engagement with the threaded element, wherein each threaded element comprises a thread to engage the locking screw of the corresponding clamp.

* * * * *